United States Patent [19]

Schewior

[11] Patent Number: 5,087,258

[45] Date of Patent: Feb. 11, 1992

[54] RING SPLINT TO SET, AFFIX AND REGULATE THE TENSION POSITION OF BONE SEGMENTS

[76] Inventor: Thomas Schewior, Fasanenweg 10, D-6903 Neckargemünd, Fed. Rep. of Germany

[21] Appl. No.: 457,745
[22] PCT Filed: Jun. 4, 1988
[86] PCT No.: PCT/DE88/00323
  § 371 Date: Jan. 19, 1990
  § 102(e) Date: Jan. 19, 1990
[87] PCT Pub. No.: WO88/10099
  PCT Pub. Date: Dec. 29, 1988

[30] Foreign Application Priority Data

Jun. 19, 1987 [DE] Fed. Rep. of Germany ....... 3720242

[51] Int. Cl.$^5$ ................................................ A61F 5/04
[52] U.S. Cl. .......................................... 606/56; 606/59
[58] Field of Search .................................. 606/53-59, 606/105

[56] References Cited

U.S. PATENT DOCUMENTS 4,584,995  4/1986  Koeneman .......................... 606/54
4,615,338  10/1986  Ilizaroy ................................. 606/58

FOREIGN PATENT DOCUMENTS 0146872  7/1985  European Pat. Off. .
0190990  8/1986  European Pat. Off. .
2832631  2/1980  Fed. Rep. of Germany .
3345276  8/1984  Fed. Rep. of Germany .
3510305  9/1986  Fed. Rep. of Germany .
2405063  5/1979  France .
2536984  6/1984  France .
85-03449  8/1984  PCT Int'l Appl. .
538710  12/1976  U.S.S.R. .

*Primary Examiner*—Robert A. Hafer
*Assistant Examiner*—Michael Brown
*Attorney, Agent, or Firm*—Peter K. Kontler

[57] ABSTRACT

A fixation device for fractured bones includes a pair of spaced arcuate supports having square or rectangular cross sections. Each of the supports is embraced by a plurality of first U-shaped holders and a plurality of second U-shaped holders, and the holders can be releasably clamped at selected positions along the supports. The first holders carry pivotable and rotatable guides, and the guides are provided with passages which receive wires to be anchored in a bone. The wires are threaded throughout their lengths and the free ends of the wires project outwardly of the guides and are provided with tensioning nuts. Additional nuts for holding the wires in position may be disposed on the central portions of the wires. Each of the second holders of one support is connected to a respective second holder of the other support by way of a strut. Each strut has slotted sleeves adjacent to the corresponding second holders and the ends of the sleeves nearest the second holders define ball-and-socket joints with the latter. The opposite ends of the sleeves are internally threaded and receive externally threaded adjusting elements designed to permit changes in the lengths of the struts. The slots in the sleeves allow the ball-and-socket joints as well as the adjusting elements to be fixed in predetermined positions by means of screws which pass through the slots. The adjusting elements of each strut are connected by a carrier including a pair of spaced columns which define a longitudinally extending gap on the strut axis. One or more anchors for additional wires are mounted on the respective carriers so as to be shiftable relative thereto. The additional wires extend through the corresponding gaps into the bone.

11 Claims, 8 Drawing Sheets

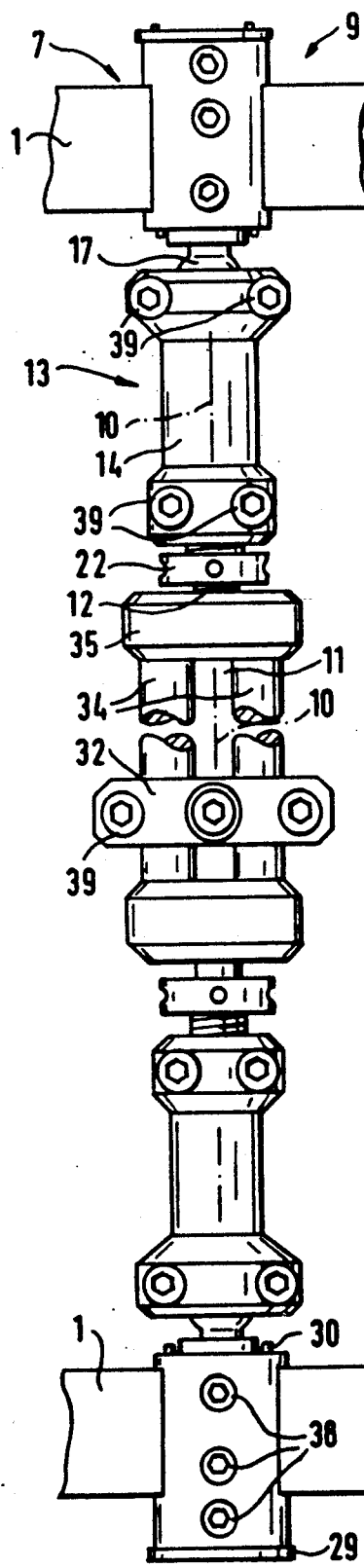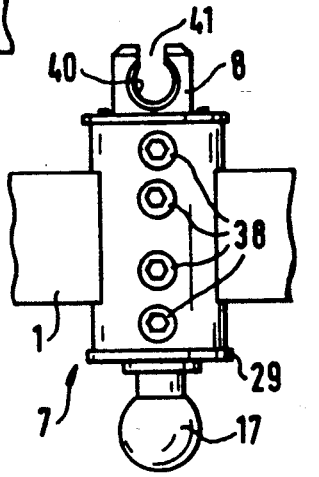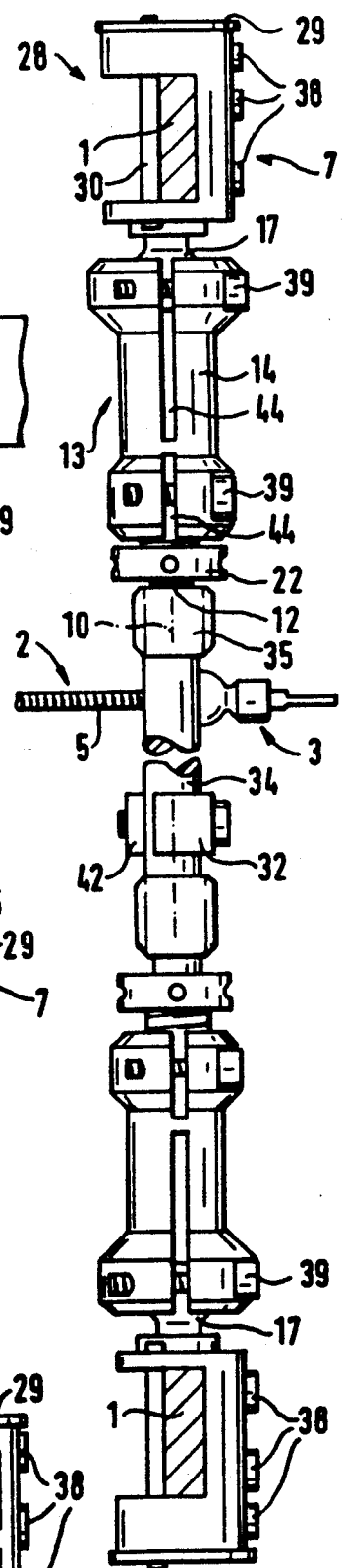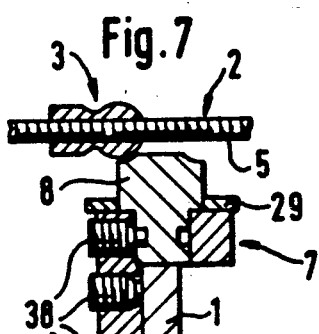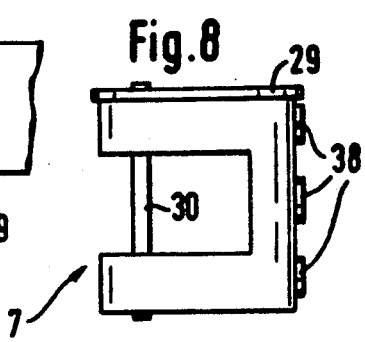
Fig. 6
Fig. 7
Fig. 8
Fig. 9
Fig. 10

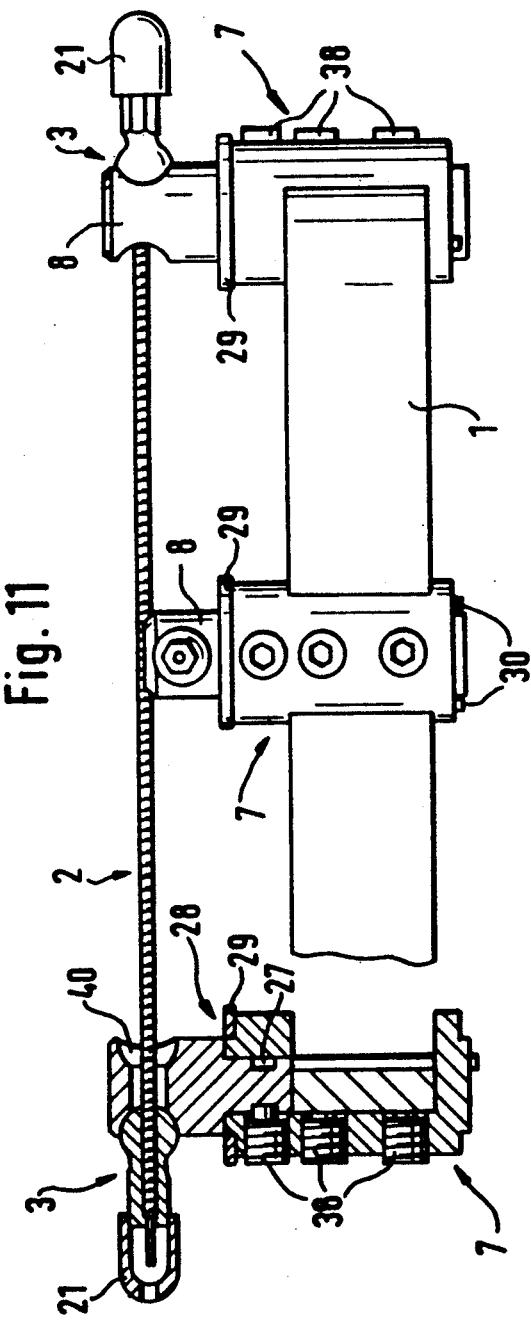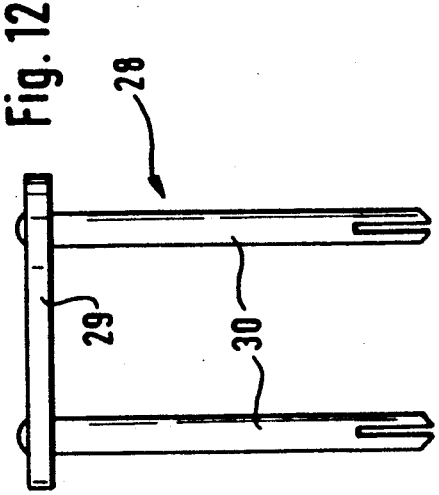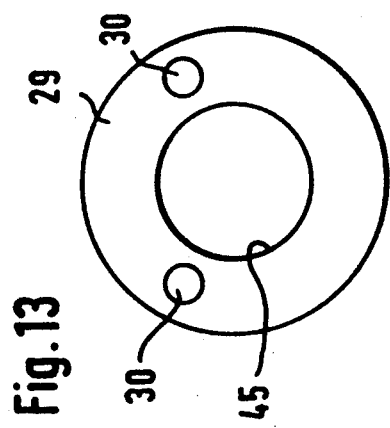

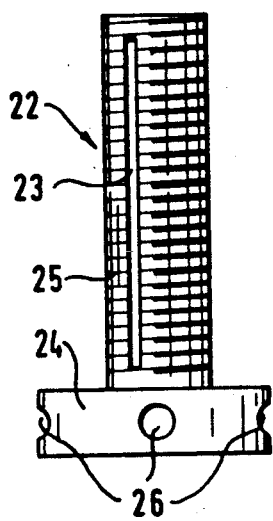
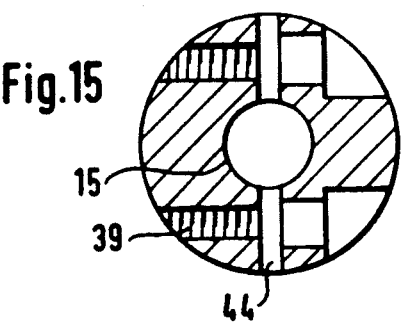
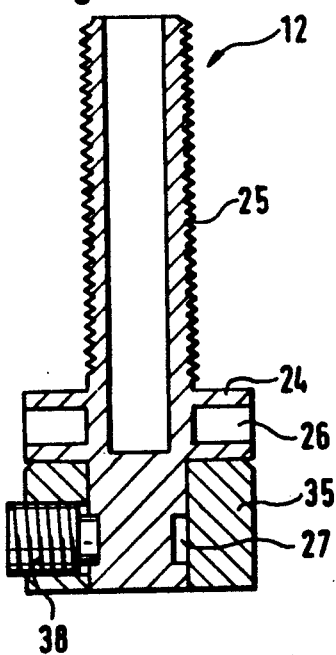
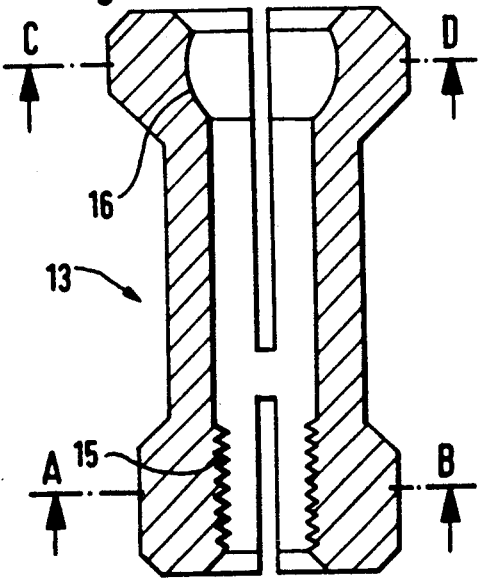
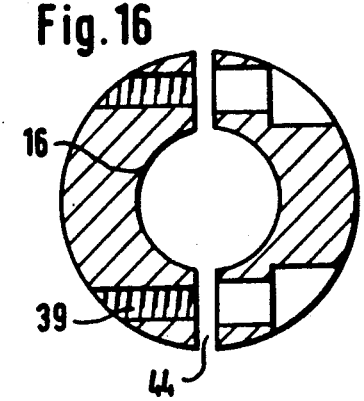

RING SPLINT TO SET, AFFIX AND REGULATE THE TENSION POSITION OF BONE SEGMENTS

FIELD OF THE INVENTION

The invention relates to a ring splint to set, affix and regulate the tension position of bone segments, consisting of wires drilled through these bone segments and, connected to these wires, of a cylindrical frame in the form of rings and/or ring sections in levels one above the other, which are connected by struts arranged at adjustable and changeable intervals and angles, and consisting of the connections of the attachment mechanisms between the rings, ring sections, struts and wires, which form these ring splint components, as in a construction kit.

BACKGROUND OF THE INVENTION

Such devices have become known as so-called compression and traction devices, especially from G. A. Ilisarov and U.S.S.R. patent No. 5387103338801/28-13 and from Italian patent No. 47890-A/82. These are splints consisting of rings and/or ring sections in which there are tension wires for bone fixation arranged crosswise in pairs or individually in each ring or ring-section level, whereby the various rings are connected to each other by means of rods, and the intervals of the ring levels are adjusted by rods of different lengths or by rods whose length can be varied telescopically. These bone fixation devices according to Ilisarov, which function by means of a cylindrical frame and tension wires, have proven to be superior to polygonal frame splints or to rod splints positioned para-axially to the bone. Just to mention the main advantages, in many situations, ring-wire splints can be fitted on an out-patient basis and under local anesthesia. They can be used to set bones three-dimensionally in a stereognostically clear manner, and secondary adjustment work can be done equally accurately with them. Without endangering the nutrition situation of the tissue and without the risk of weakening the stability, any wires can be subsequently attached, removed or replaced. Unlike the rigidly anchored rod and frame splints, the treatment with such ring-wire splints is designed as a prolonged, continuously progressing operation process. Failures that would have been ascribed to unsuccessful or improperly performed operations at a certain point in time are inconceivable here because of the process characteristic involving the constant possibility of progressive correction. Ilisarov's ring fixation techniques are largely subordinated to the biological healing process since, method-related, early stress of the limbs provides relevant information on the processes of callus formation and bone transformation, as they occur within the context of natural self-organization and autoregulation. After all, the flux of force is maintained as a function of the stress for such concentrically positioned fractures or osteotomies, whereupon nature, within the scope of self-organizational and autoregulatory consolidation, generates distinguishable building material in the fracture or osteotomy zone and arranges it stress-specifically, in a locally selective manner, in response to compression and tension. Since the ring splints, as an external stabilization frame, are stable with regard to jolting, bending and torsion, thanks to their cylindrical structure, and since flexible bone-penetrating wires serve as very stable anchoring bearings, it is possible to stimulate certain tissue-forming and reshaping processes within the scope of the physiological reaction spectrum, processes which are regulated by the adaptable flexibility of the wires; consequently, new bone formation can be controlled very accurately for the sake of therapeutic repair and regeneration.

In principle, the Ilisarov ring appliances can be fitted for most stereometric situations. However, many changes in shape and tension cannot be carried out with adequate precision and, in view of the frequency of the necessary correction steps, they cannot be carried out as simply and quickly as would be desirable. Moreover, the inevitably inconsistent manipulation of the original ring splints and the various replicas make it impossible to reliably assure the consistency necessary for the progressive healing procedure of this externally and dynamically affixed osteosynthesis therapy.

A ring splint with improved flexibility has been disclosed in West German patent DE-OS 3,439,795, which relates to a device to set bone segments and/or bone fragments, with which device the connection rods between the rings are connected to the rings in such a way that they can be pivoted within predefined but narrow limits in all directions and can be secured in any pivoted position, whereby the intervals between the adjacent rings in different levels can be adjusted independently of the selected pivot position of the rods; however, not the entire circumference of the rings is available for affixing the connection rods, but rather, the attachment is limited only to certain places along the circumference of the rings, which are provided with a number of boreholes. This device allows a certain dislocation-free neutralization of the forces being exerted, but nevertheless, in spite of its improved three-dimensional adaptation possibilities, it is not able to sufficiently fulfill the prerequisites of an operation technique aimed at natural causal histogenesis. First of all, the rings, as in the Russian device, are transversally positioned surface sections with a cumbersome, large outer circumference. Second, the connection rods between two rings can only be affixed at certain predefined places along the rings, as a result of which it is not possible to slide the ends of the connection rods along the rings completely at will. Third, the spatial wire control for the tension wires of the known appliance is insufficient because the tension wires can be placed under tension practically only in the direction of the diameter, and an off-center wire position is associated with a risky bending of the wires. Fourth, in order to tighten and retighten the wires, special wire stretchers are needed, which have to be made specially for this stretching procedure. Fifth, with the known ring splint, it is not possible to use the connection rods as torsion-free, axially supported anchoring sites for the tension wires to be stretched between the ring levels. Sixth, there is only the possibility for frictionally engaged and not linearly engaged clamping attachment in the pivot bearings of the rods.

Objects of the Invention

Therefore, the invention is based on the overall objective of providing an improved ring splint of the type mentioned above. This objective is divided up into three partial tasks, which are of a stereometric, a dynamometric and a tactical nature.

The stereometric task calls for continuous adjustability of the lengths of the struts, as well as of the angle settings of the struts with respect to the rings or ring segments, for the random selection of any place on the rings to fasten the strut and wire attachments, and for the random selection of any place for attaching the wires between the rings and on the struts themselves.

The dynamometric part of the task calls for the possibility of selecting all of the tension positions that are to be created between the ring splint parts themselves and likewise of selecting all of the tension positions that result from the connection between the ring splint on the one hand and the bone tissue or the soft tissue on the other hand, in such a way that these tension positions can be established continuously and without the need for an additional tensioning device.

The tactical part of the task calls for such simplicity of use that, when the ring splint is applied at the start of the therapy as well as during the entire therapeutic fixation phase, all of the stereometric fixation measures and all of the dynamometric tensioning measures can be carried out with just a few similar and recurring hand movements of adjusting and tightening all of the moving and force-absorbing parts, whereby carrying out the measures comprising subsequent insertion, removal or replacement of fasteners, ring segments, struts and wires should each be possible separately and in the ring-radial assembly direction—that is, without interfering with the rest of the splint arrangement.

SUMMARY OF THE INVENTION

A first decisive advantage of the device according to the invention stems from the wires, which are designed as threaded wires with continuous threads to screw on tension and position nuts. As a result, it becomes possible to tighten the wires without a need for the use of special external tension devices. In order for ring splints to fulfill the biomechanically oriented therapy concept, they must be stereometrically and dynamometrically adaptable to the natural healing processes; this means that, during the treatment process, it must be possible to regulate the position as well as the tension of every single wire. Since the method prescribes that these corrections must often be made in small increments—usually on a daily basis—the fact that the tension can be regulated by simply turning the wire-tension screws according to the invention means that this is the first time that progressive osteosynthesis techniques can be implemented in actual practice.

Moreover, the threading of the wires is advantageous because, during the wire drilling, which can be carried out in the opposite direction to the direction of the thread, in other words counterclockwise drilling for a clockwise thread, the wire threads effectuate the return of the bone "sawdust" created by the drilling and also because, in this manner, the borehole walls are protected from excessive drilling heat by the blood and tissue fluids.

The threaded wires are also advantageous because it is possible to screw the position nuts on at any desired place along the wires and, according to the invention, these position nuts have a polyhedron-shaped, angular surface design and lock in place, thus dispensing with the need for a set of special "olive wires"; "olives" are the nuts used by Ilisarov, which have smooth surfaces and which are attached to the wires by a metal-to-metal connection.

Finally, the thread configuration is also advantageous because it makes it possible to position the wires over the spherically supported tensioning nuts in pivoted and yet buckle-free tension positions.

Another decisive advantage of the device according to the invention stems from the wire bearings to connect these threaded wires with the rings and ring elements or with the struts since they consist of flush, U-shaped clamping sliders that can be slipped onto, removed from or locked along the circumference of the rings or onto the struts in the direction of the radius of the ring or in a direction rotated by 90 degrees from this radius and, even when they are locked on, they can be freely slid or else clamped. If one looks at the device according to the invention from an anatomical and operation-mechanical point of view, it can be seen that the advantage of the free sliding properties of the U-sliders instead of the conventional restriction to wire fasteners in predetermined places lies in the fact that this free placement selection always offers the possibility of avoiding anatomically risky penetration sites and penetration directions when the wire is drilled into place.

In the case of a secondary measure, such as wire replacement and new installation of a wire, finely adjustable wire placement is also an advantage. From a dynamometric point of view, this free selection of the wire positions has a significant advantage, since tension-free wires must always be the initial situation for fitting a finished ring-wire splint, when stereometric and dynamometric procedures are to bring about only therapeutically successful tension loads but no other tension loads, and to transmit these loads to the bone fragment configuration.

Thus, due to this possibility of continuously sliding the U-sliders, it is advantageously possible to precisely bend the wires which have already been drilled by subsequently repositioning the U-sliders, in order to enhance the wire straiqhtening on the basis of this bending by increasing the wire tension with which the straightening of the transfixed bone segment can be guided perpendicularly to the wire direction. In this manner, shaping as well as changes in the flux of force can be precisely adjusted spatially or else adapted to the regenerative bone and connective tissue products that are growing and organizing specifically in reaction to the load being exerted.

. Moreover, another advantage of these wire bearings according to the invention is the fact that wires which are bent or whose bending continuously changes as the tension increases do not buckle since they can be inserted through tension bearings of selectable lengths which have spherical bearing surfaces and which are detachably connected to the U-sliders and, once this has been done, the wires can also be supported so as to pivot three-dimensionally. This pivoting bearing capability of the threaded wires and their tensioning in a buckle-free pivoted position is only possible thanks to the design of the tension nuts with their spherical bearing surfaces according to the invention. Advantageously, these ball headed tension nuts, with their ball heads facing towards the outside, can also serve as protection against injury. In contrast, in the case of the conventional wires, it is necessary to bend the ends inwards, which makes the wires practically useless for later tension adjustments.

It is also advantageous that these perforated bearings can be rotated around their longitudinal axes, can be secured in any rotated position and can be replaced. Thus, as the need arises, shorter perforated bearings can be replaced with longer insertable perforated bearings and vice versa. If it should become necessary to replace the wire and also to replace the perforated bearings, the new wire drilling can once again be made in an anatomically safe place, which can deliberately be a certain distance from the bone penetration site which will no longer be used.

Another ever-present advantage of the pivoting perforated bearings is the fact that sleeve elements, which function as a hole gauge, can be slipped in and, during the drilling procedure, can establish the drilling direction in such a manner that every wire, running precisely parallel to the plane of the ring, can reach the opposite perforated bearing without having to be bent to make a correction. If only the existing perforated bearings of a wire are replaced with perforated bearings of a different length while the U-slider position remains the same, then it is possible to bend the wire precisely in the direction of the ring splint height or of the longitudinal axis of the bone, something which can be therapeutically utilized by increasing the wire tension so as to straighten the wire for height regulation as well as for influencing the position stability of bone segments which are transfixed in such a way.

Another important advantage of the wire bearings according to the invention lies in their U-shaped symmetry. If need be, it is possible to tighten a wire in one and the same U-slider at both sides of a ring or of a strut. This symmetrical position, which also exists for the tension forces, has the effect that the torsions in the opposite direction stemming from the wires neutralize each other, so that, as a result, undesired deformations of the ring splint frame can be avoided and high, therapeutically useful tension loads can be produced.

A pertinent advantage is also the option of using the U-slider for securing the strut bearings according to the invention. In order to assemble the splint, all that is necessary is to use insertable coupling elements, which are inserted into correspondingly shaped ends in the sockets of the U-sliders and in the clamp fasteners of the strut bearings. In an advantageous manner, this technique of fastening the struts makes it possible to attach one or two wires to one and the same U-slider by means of one or two perforated bearings, to attach one or two strut bearings by means of one or two coupling elements, or to attach a mixed combination of one wire bearing and one strut bearing via the U-slider to a position on the ring.

The advantages of this combination capability lie, on the one hand, in the fact that this results in a far greater variety of fitting possibilities while, at the same time, reducing the number of assembly sites per ring and, on the other hand, in a considerable reduction in weight, thanks to the smaller number of U-sliders. The strut attachment by means of the U-sliders makes it possible to select any site along the ring circumference as a place to put a strut bearing. This is necessary in that the attachment mechanisms of the wires must always have the best possible placement, whereas the selection of places to attach the struts have to accommodate and adapt to the fact that the wires have priority.

Another advantage is that it is not necessary to completely dismantle the struts—which would unstabilize the ring arrangement—in order to implement diverging transverse shifting of the struts, but rather it is only necessary to loosen the clamping of the U-sliders on the ring, while they remain frictionally engaged.

An advantage for simple attachment and replacement of individual struts or all of the struts, usually within the scope of the progressive length adaptation, is the fact that the struts, together with the U-sliders, can be fastened onto the rings in the ring-radial assembly direction and can be removed from these rings in the opposite direction. Therefore, since penetrating assembly between the rings and struts is avoided everywhere according to the invention, the dismantling steps on the ring splint are very simple, and it is possible to reliably avoid risks to stability as well as unintentional motion of the bone fragments, even during intercurrent, progressive reconstruction phases that become necessary during the course of the therapy.

Another decisive advantage is the design of the struts according to the invention with gap-shaped recesses in the strut axis and with replaceable, spindle-shaped sections to fit them onto ring levels whose distance can change. These openings can be lengthwise slits between two partial struts or a row of perforations located in the center line of the struts, through which bearing wires as well as pivoting fixation and control wires can be fastened.

An essential stereometric advantage lies in the resultant wire positions which are possible due to the interaction of the strut slits and can be freely selected with respect to their place and direction in the intermediate area between the rings by the rotatable spindle-shaped strut segments and by the wire tension nuts with pivoting bearings.

An important advantage of the gaps along the longitudinal axis of the struts can also be seen in the fact that the penetration points of the wire-tension forces lie on the center line of the struts, so that no torsion is exerted on the struts by the wire tension and thus, no undesired movement of the bone fragments which are attached to these wires can occur either.

In addition to the spindles being axially rotatable and capable of being clamped like a chuck, the replaceable spindle-shaped strut segments also entail the advantage that, in conjunction with the longitudinal bearings of the struts still to be described, it is possible to undertake rough length adjustments of the struts by replacing spindles and fine length adjustments by means of telescopic turning of the screws.

A decisive advantage, one which is necessary to fulfill all of the requirements of the technical task, is that the strut bearings to connect the struts with the rings and/or ring sections have tension sleeves for flush clamping and continuous adjustment, which make it possible to perform lengthwise as well as three-dimensional angle-adapting adjustments of the struts, whereby the adjustments for linear degrees of freedom can be carried out separately from the adjustments for rotational degrees of freedom. The surface clamping attachment, which has to be made slip-proof against shearing forces, is achieved by chuck-like slitting of the tension sleeves, thus forming two half shells, both at the length-adapting axis bearing as well as at the angle-adapting ball bearing. Tension bolts which are supported in aligned flange boreholes of the tension sleeves account for the necessary clamping tensions with an advantageous ring-radial access path.

It is especially advantageous that the supported ball-and-socket-joints can be handled in different ways, depending on the tension force of the tension bolts, and that they are replaceable or freely moveable, but secured against being dislocated, or intentionally hard to move due to higher friction forces, or completely slip-proof due to strong surface pressure.

The clamping bearings of the tension sleeves have the special advantage that no counter nuts have to be dealt with in difficult work procedures in order to secure the spindles against rotation and to axially stabilize them, but rather that, just like in the adjacent ball bearing, stable clamping tensions can be achieved by means of the effect of tension-bolts. Another favorable aspect of the chuck-like thread clamping is the fact that a wobble-free fit can be produced, even when the spindles are only supported over a short distance.

It is also advantageous that, due to such a chuck-like bearing arrangement, even in the case of concentrically intermediately supported sleeves, the necessary clamping forces can be applied to a central axis if, in the case of the screw sleeves, these are provided with longitudinal slits according to the invention.

A likewise crucial advantage of the ring splint according to the invention lies in the fact that the design of the rings and ring sections is in such a shape that their wall cross section is square or upright-rectangular and in that they are made of fiber embedded in a matrix, which is continuously wound unidirectionally in the direction of the circumference.

In the case of such a ring designed as cylinder segments, it is advantageously possible to keep the walls thin; this can be done, first of all, when a fiber-matrix material composition is used which, due to the combination of fibers with great tensile strength and compression-proof embedding material, is characterized by high elastic restoring force without plastic permanent set and, secondly, when such a cylinder height is selected that torsional stability is ensured. In an advantageous manner, it is possible to make use of the fact that the torsional stability of a ring is proportional to the height of this ring elevated to the third power. Thus, these rings can be made to be relatively low and to have relatively thin walls, without losing any of their stability.

Another advantage of this ring and ring segment design is that they lie close to the limbs, in other words, their diameters can be kept small. Thus, in contrast to conventional ring splints with flat rings requiring large diameters, the ring splint according to the invention does not take a lot of space and is far less cumbersome for the patients. Thanks to such rings, in an advantageous embodiment, the patients can easily wear the ring splints even under pant legs or shirt sleeves. The selection according to the invention of a square cross section has the advantage that the U-sliders to be clamped can also be affixed in a position that is rotated by 90 degrees, which translates into a considerable expansion of the stereometric fitting possibilities.

It is also advantageous that ring segments can be combined to form full rings by means of a stabilizing snap-on closure. It has turned out to be favorable that threaded wires and/or struts can also be attached to such a closure, which joins the ring sections to form the full ring, thus once again saving space on the ring circumference and reducing the weight.

Another advantageous embodiment is to be found in the design of the screw caps which can be screwed onto the ends of the wires as protection against injury, and which can be taken off when a wire-drilling clamping chuck is attached, but which can be left on when the tension nuts are manipulated. The advantage is that the wires do not have to be bent in order to safeguard against injury. Consequently, they remain intact for re-use.

Another advantageous embodiment lies in the design of flange-bearing spindles with a threaded section, with key faces and/or a hole circle on the flange and with a ring groove on the end, since these spindles can be joined with the gap-shaped strut sections consecutively in the order of positioning, locking and rigid clamping, so that, due to the telescopic interaction of such spindle-shaped, supplemented struts with the above-mentioned sleeve-shaped strut bearings, the length adjustments can be made at the ring-level distances to be bridged. After the coupling pivot bearing to connect the strut sections has been used in order to carry out this length adjustment by turning the adjustment screw that grasps the ring groove and, if necessary, after the rigid securing spindle clamping has been established, it becomes possible to make screw-type length adjustments either by turning the strut bearing while loosening both chuck-like bearings or by turning the spindle while loosening both of its bearings on the ends.

An additional advantage of such replaceable spindle-like strut ends can also be seen in the fact that the assortment of available, lengthwise-perforated or lengthwise-slit strut sections can be reduced, since the rough length adjustment of the struts can be regulated by means of an assortment of spindles with different lengths.

A special advantage in terms of handling this splint lies in the locking pins to effectuate form-fit clamp tension between the U-sliders on the one hand and the rings or struts on the other hand. These locking pins close the U-openings of the sliders and, by means of the pivots, implement spatially fitting adaptation tensions for a wobble-free fit of the U-sliders.

It is possible to reposition the pins by splitting the pivot ends which, when they are in their inserted position, create split-pin friction in the case of slightly divergent halves, thus providing protection against falling out. These slits have an advantageous effect because a clamped fit of the locking pin can be achieved, something which is easy to establish and equally easy to change.

Another embodiment of the invention, which is especially advantageous from the dynamometric point of view, results from the design of threaded spindles which can be attached para-axially to the struts, and onto which adjustment nuts can be screwed which, when turned, can determine the height adjustment of the wire bearings. These height adjustments of the wires positioned between the ring levels, which have to be made during the course of the treatment, produce a change in the bending and tension of the wires of one and the same bone fragment lying in adjacent levels. In this manner, a highly precise adjustment of the position stability of the bone fragments is achieved and, within the scope of the phases of the natural autoregulatory ossification and bone-transformation processes, it is possible to carry out specific wire-tension adjustments, as well as to make constant regulations of the amount of tension in adaptation to the natural healing process.

It is very advantageous that, thanks to such a spindle-guided transport mechanism, wire-controlled bone-fragment movements can be carried out as so-called bone-shift plastic-surgery.

A special advantage of the struts, which are designed as a frame consisting of two carriers running parallel to the longitudinal axis and two frame legs positioned at right angles to the carriers, can be seen in the fact that the tension nuts under tensile stress can be supported on the smooth, gap-forming walls of the carriers without sliding through in the direction of the tension and without a need for specially supporting perforated bearings, and in the fact that, in the case of a therapeutic length-change process of a limb, these tension nuts can move along in the tension direction, connected to the wire they support, without an increase occurring in the wire tension, while they nevertheless still contribute to the neutralization of dangerous lateral bending of the fragment and fragment torque motions in the opposite direction.

An advantageous greater freedom with regard to spatial assembly is available if necessary—especially for combinations of a pair of bones—when, during installation of threaded wires in the area between the levels of two rings, pivoting and linked frame sections are joined to form struts to support the threaded wires. According to the invention, cylindrical coupling axles are suitable to connect these partial strut sections, and these axles can be locked and clamped by ring grooves that run around both ends of the cylinder. In this manner, such frame-like strut frames, equipped with appropriate pivot bearings, can be assembled, turned in the opposite direction and also locked so as to remain rigid. This makes it possible, starting with a strut, to drill at a selectable height and pointing in various horizontal directions and, starting from such divergent positions, to pivot the wires independent of each other.

As a result of the simplified handling according to the invention, special application advantages arise from this ring splint:

The simplicity of the first fitting and of each repositioning, which is due to the modular design of this ring splint, makes it possible to carry out the operation more quickly so that, even in difficult cases of osteosynthesis, out-patient treatment can be considered, possibly even with local anesthesia. This means that, thanks to this invention, there are application possibilities that are not usually associated with ring splints, but that could fall into their range of actual application: namely, it could be used in military medicine already on the front line at the main first-aid treatment site, furthermore for large-scale use in disaster areas and in case of mass traffic accidents, both of which cases involve numerous and multiply injured persons as well as extremely severe injuries for which the life-saving therapy approach occurs under the aspect of triage guidelines for providing care, where time-consuming bone operations involving large blood loss are impossible due to the risk of death. The faster an operation technique can be carried out with a ring splint with versatile threaded wires to set a fracture, and the less traumatic it is to the soft parts and to the bones, the lower the risk of infection and the less need there will be for conserved blood, which always entails the risk of the spread of infectious diseases.

Finally, there is a considerable production advantage that arises from the preferred embodiment of the ring splint according to the invention: most of the components, due to the demand for unhindered three-dimensional flexibility, have been designed as turned parts and can be made on automatic, computer-controlled lathes, so that the variations in the embodiments that arise within the scope of the invention in the practical trial phase can be implemented by changing the programming of the automatic lathe and it is not necessary to go through the expensive step of making patterns.

BRIEF DESCRIPTION OF THE DRAWINGS

Examples of the invention are shown in the drawings and subsequently described. In the drawings:

FIG. 6 is a front view of a wire bearing placed on a ring section with a perforated bearing and with a coupling element, both of which are held on the ring-U-slider of the wire bearing FIG. 7 is a vertical section through a wire fastener with perforated bearing and coupling element in the locking position, whereby all of the section hatching has been left out for the sake of clarity FIG. 8 is a side view of a ring-U-fastener placed on a cut-open ring, whereby the cross section of the wall of the ring is square FIG. 9 is a front view of a strut, consisting of a frame section with two carriers framing a longitudinal gap, of two screw sleeves supported on this frame section which extend into a strut bearing and of a coupling element, which creates the ball-joint connection to the ring-U-fasteners on each side FIG. 10 is a side view of a strut attached to two rings according to FIG. 9, whereby the rings are cut open FIG. 11 is a partly sectional front view of a splint ring with three wire bearings FIG. 12 is a side view of a locking pin for the ring FIG. 13 is a top view of a locking pin inserted into a ring-U-fastener FIG. 14 is a vertical section through a strut bearing-tension sleeve with a ball bearing and a sleeve bearing, which are arranged at a distance from each other FIG. 15 is a horizontal section through the sleeve bearing of FIG. 14 as seen along the line A-B with a representation of the diametral wall slits and the paired tension-screw bearings FIG. 16 is a horizontal section through the ball bearing of FIG. 14 as seen along the line C-D with a representation of the diametral wall slits and the paired tension-screw bearings FIG. 17 is a longitudinal view of a screw sleeve with an external thread, longitudinal slits (only one shown), flange and hole circle for socket wrench FIG. 18 is a longitudinal section through a threaded spindle with an insert-type hole circle in the flange and with an insertable end having a ring groove, which is supported in the locking position in the transverse frame bar

DESCRIPTION OF THE PREFERRED EMBODIMENTS

Figure 1:
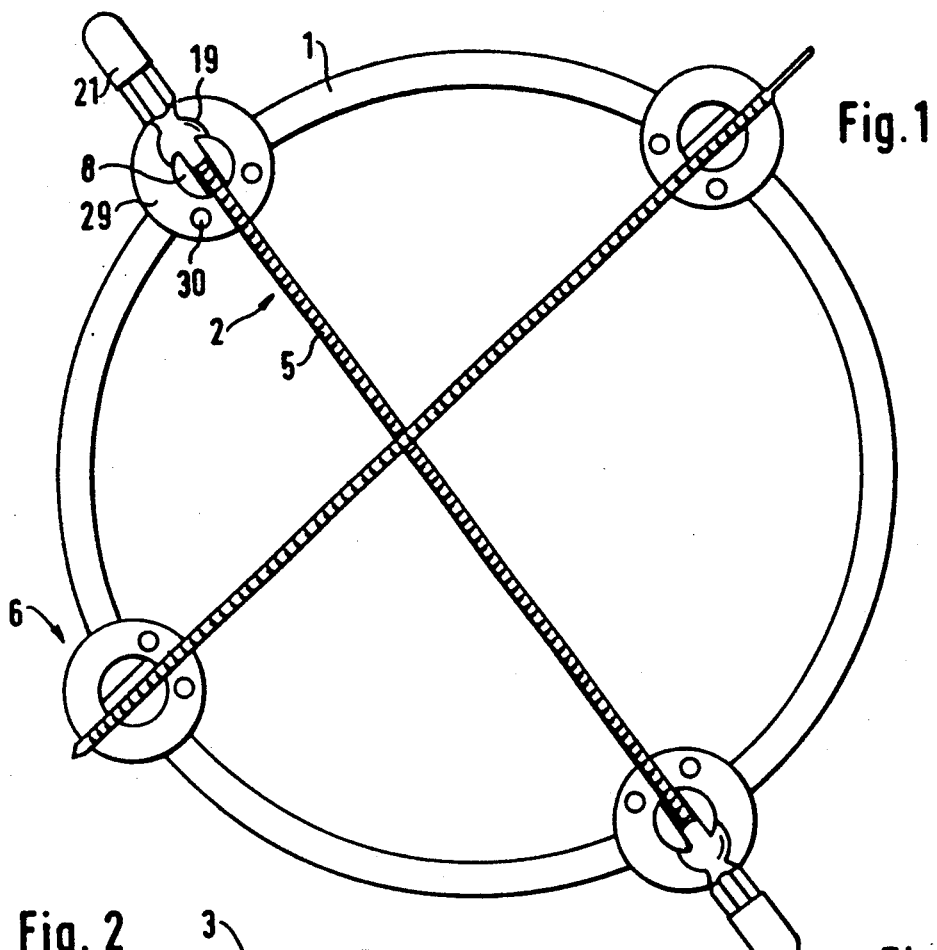
FIG. 1 is a top view of a ring-splint ring, showing two wires that cross each other and the wire bearings that hold them onto the ring

In the figures, the same parts are labeled with the same reference numbers. FIG. 1 and FIG. 11 show the top view and front view of a ring-splint ring 1. The positioning on this ring of wire bearings 6 is illustrated. The wire bearings 6 consist of a ring-U-fastener 7 and a perforated bearing 8—or, in the case of a design symmetrical at the level of the rings 1, of two perforated bearings 8 across from each other. The attachment of the ring-U-fastener 7 to the ring-splint ring 1 is done in such a way that the ring-U-fastener 7, with its open U-side facing the ring 1 as shown in the vertical section through the left-hand U-fastener 7 of FIG. 11, is put in a form-fit manner onto the ring 1 at a place defined by the overall assembly plan or else at any desired place, and subsequently blocked by inserting a locking pin 28.

This locking pin, shown in FIGS. 12 and 13 in a side view and a top view, respectively, consists of a carrier plate 29 and of paired pivots 30 which are attached to this plate, extend out over the ring 1 and have free ends which are inserted into the ring-U-fastener 7. After this insertion assembly step has been carried out, the wire bearing 6 can at first be freely slid along the circumference of the ring. The locking pin 28 does not fall out of the receiving, aligned boreholes of the U-leg of the ring-U-fasteners since the ends of the pivots 30 have slits which can be bent for the purpose of creating an adequately tight-clamping fit of the locking pin 28. After the U-fastener is locked, it is clamped onto the ring 1 in such a way that the stud screws 38 that can be screwed into the base of the U's of the ring-U-fastener 7 are turned until a force-absorbing fit is achieved on the ring. In this manner, as a result of a slight outward movement of the ring-U-fastener 7, a double line-shaped frictional connection, which generates a stable clamping fit, arises between the pivots 30 and the inner side of the ring 1. This clamping fit can simply be loosened by means of the stud screws 38 without any further disassembling steps and can be re-established after the U-fastener has been slid to another position.

In one leg of the ring-U-fastener 7, as shown in FIGS. 9, 10 and 11, or else in both legs, as illustrated in FIGS. 6 and 7, perforated bearings 8 and/or coupling elements 17 are held in such a way that they can be clamped and locked by means of the stud screws 38. They can be locked or unlocked for removal or for replacement by screwing the stud screws 38 to the proper depth into the ring groove 27 and they can be held rotatably or rigidly blocked in a determinable rotation position. During the fastening procedure of the perforated bearings 8 and of the coupling elements 17, the central perforation 45 of the carrier plate 29 of the locking pin 28 assures the unhindered penetration of the components to be inserted into the ring-U-fastener 7. This fastening possibility also exists with the locking pin-carrier plate 29 in connection with the design of a ring-U-fastener 7 with an attached ball head coupling (same shape as the ball head of the coupling element 17), as shown in FIG. 10.

Figure 31:
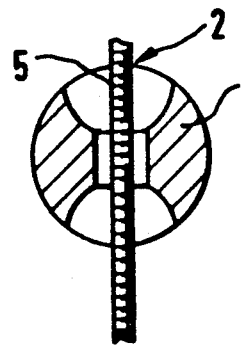
Figure 29:
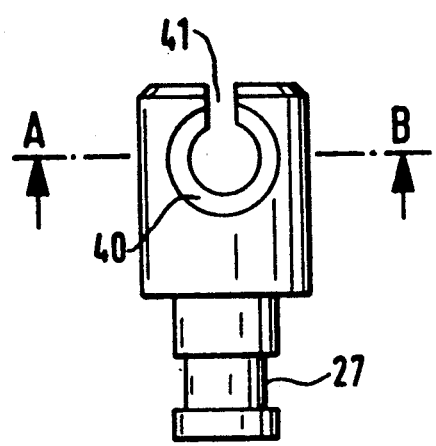
Figure 30:
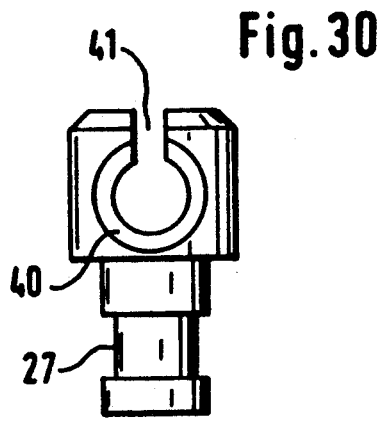

FIGS. 29, 30 and 31 show embodiments of the perforated bearings 8. The perforated bearing 8 consists of a cylinder part which is adjacent to a tapered part, likewise in cylindrical form, which has a ring groove 27 at its lower end. The distance between the ring groove 27 and the bearing shell 40 of the perforated bearing 8 can be different, and thus, by choosing the perforated bearing accordingly, the necessary height distance of the threaded wires 2 from the appertaining ring can be selected. In a symmetrical manner, bearing shells 40 can be inserted into the perforated bearings 8 at the entry point as well as at the exit point of the threaded wires 2, which facilitates the assembly since the perforated bearings 8 can be rotated in any way.

Figure 2:
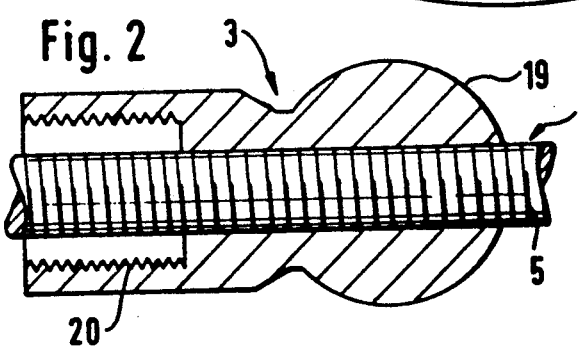
FIG. 2 is a longitudinal section through a wire tension nut which is screwed onto a threaded wire
Figure 3:
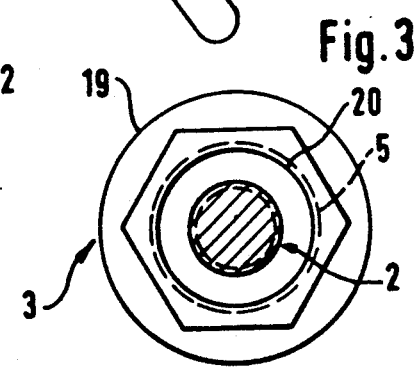
FIG. 3 is a top view of a wire tension nut

In a longitudinal section and in a top view, FIGS. 2 and 3 show, respectively, a wire tension nut 3 which is screwed onto a threaded wire 2. The wire tension nut 3 has a spherical bearing surface 19 with which it is supported in the bearing shell 40 of the perforated bearing 8 in such a way that it can pivot, as shown in FIG. 31. The threaded wires 2 can be laid in the bearing shells 40 and removed from them via the slits 41 and end faces of the perforated bearings 8. The interaction of the sliding ring-U-fasteners 7 with the rotating perforated bearings 8 and the supported wire tension nut 3, which pivots, provides a spatially virtually unlimited adjustability of the threaded wires 2 with respect to their anatomically oriented placement and penetration direction, which must be selected carefully in view of the sensitive nerve and blood vessel structures.

The outer ends of the wire tension nuts 3 are equipped with an internal threaded section 20 for attaching protective caps 21 whose diameters are restricted in such a way that they can be inserted into hexagonal hollow keys which grasp the hexagonal surfaces of the wire tension nuts 3. As an alternative, the protective caps 21, as shown in FIG. 1, can also be slipped over the wire tension nuts in a form-fit manner, even with larger dimensions, whereby edge slits effectuate an adjustable clamping fit of such protective caps 21. Instead of separately manufactured protective caps 21, it is also possible to screw another wire tension nut 3 onto the threaded wires 2 in a reversed way, thus countering the already present wire tension nut 3, so that the round tension nut bearing surface, now facing towards the outside, can serve as protection against injury on the wire ends.

Figure 4:
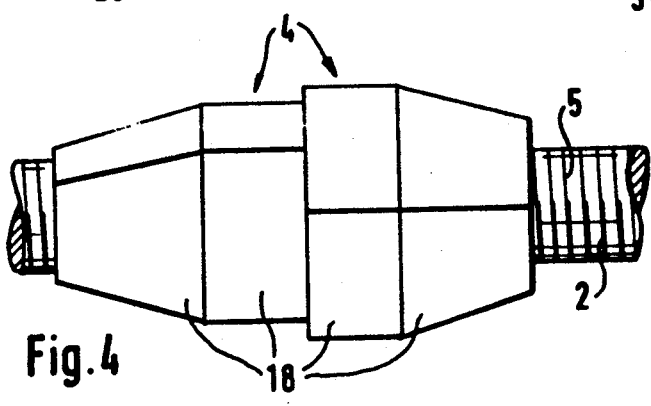
FIG. 4 is a side view of a pair of polyhedron-shaped position nuts on a threaded wire in a random rotation position
Figure 5:
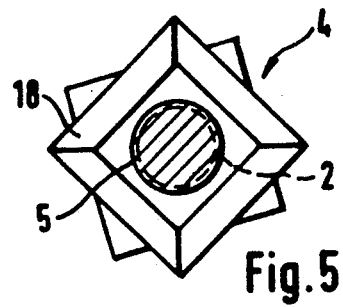
FIG. 5 is a top view of the nuts of FIG. 4 in the opposite rotation position
Figure 21:
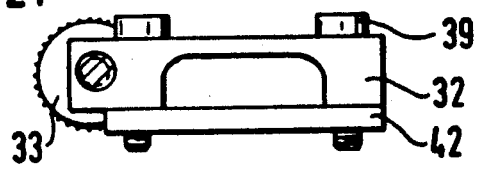
FIGS. 19–22 are views of a transport mechanism—para-axially supported on the strut frame—for the strut-wire bearings with threaded spindles and the combination of position nut and clamping, wire-guiding strut-wire bearing to adjust the height of the wire bearings
Figure 19:
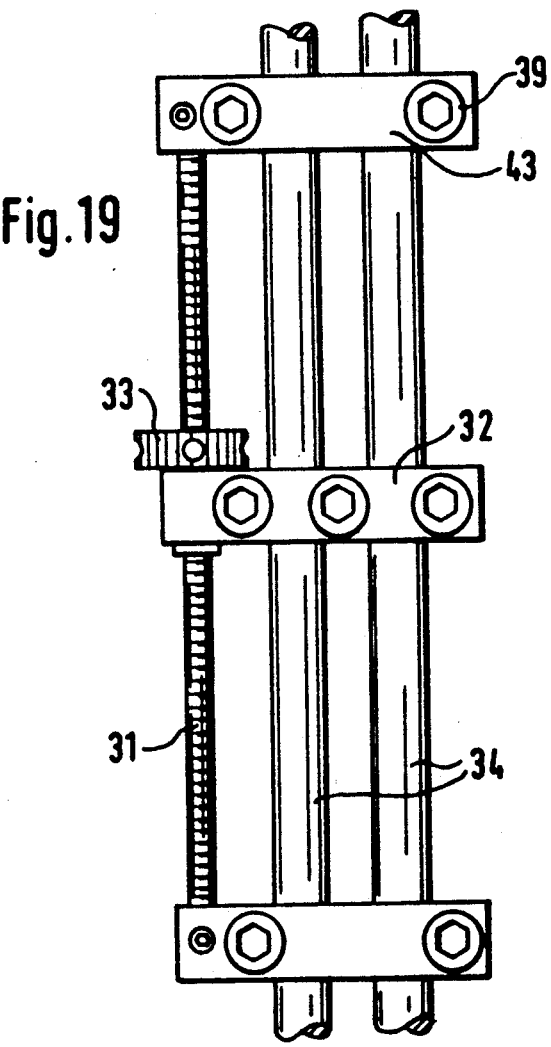
Figure 20:
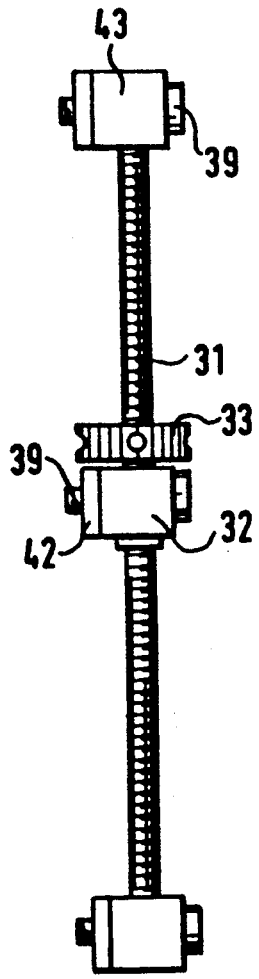
Figure 22:
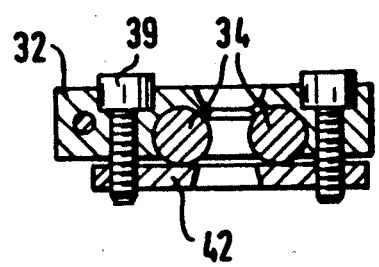
Figure 24:
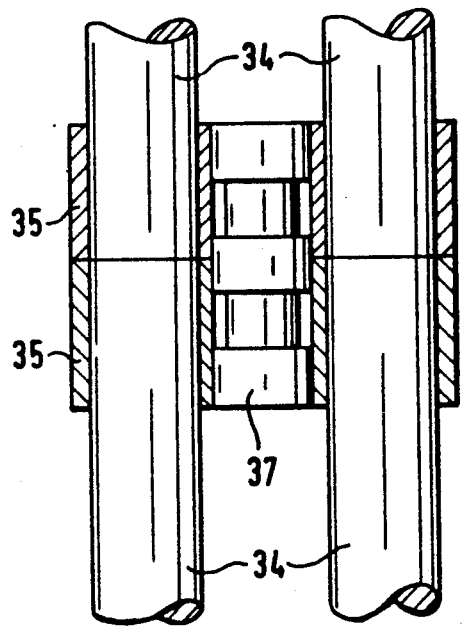
FIGS. 23–26 are views of the connection, which can be put together, rotated and attached, of two frame-shaped strut sections, which are made by means of a coupling axis
Figure 26:
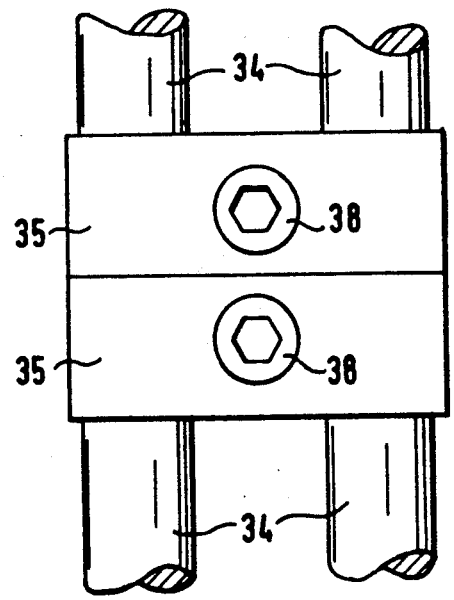
Figure 25:
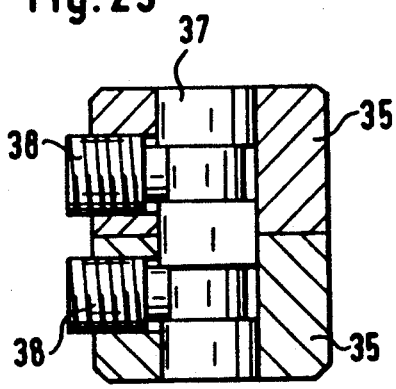
Figure 23:
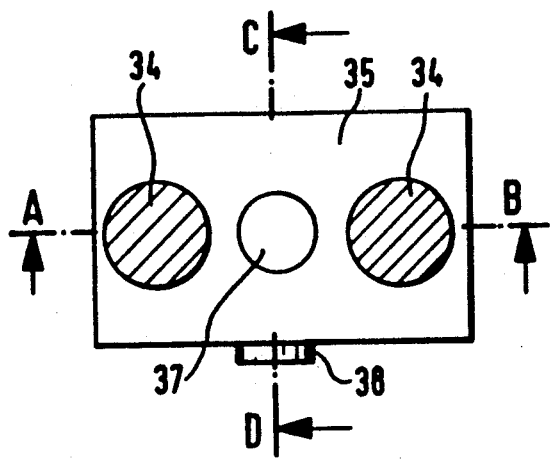

FIGS. 4 and 5 show a side view and a top view, respectively, of wire position nuts 4 which have longitudinally oriented, polyhedron edges on their surfaces and which can be locked with their face surfaces against each other. They can be firmly attached anywhere on the threaded wires 2 by means of locking against each other. They serve to guide the wires in the longitudinal direction, whereby the polyhedron edges, which converge on the face ends, have frictional contact with the bone entry points of the threaded wires 2, thus holding these threaded wires in a rigid position during the wire-tightening screwing procedure.

FIGS. 7, 8 and 11 show, among other things, that the cross sections of the ring walls can be upright-rectangular or square, so that, in addition to the preferred horizontal assembly of the ring-U-fastener 7 to be carried out in the ring-radius direction, as is the case with the upright format of the ring-wall cross sections, it is also possible to select an insertion that is rotated by 90 degrees, normal to the ring plane and coming from above or from below. The square ring-wall cross section leads to consistent embodiments of the ring-U-fastener with respect to the connection adjustments of attachable perforated bearings 8 and coupling elements 17.

FIGS. 9 and 10 show the preferred embodiments of the various sections of the struts. By means of the ring-U-fastener 7 and the coupling element 17, the struts can be supported in such a way as to be pivoted between the rings 1 in the ball bearings 16 and in such a way as to be height-adjustable by means of the sleeve bearings 15 and the screw sleeves 22. The wall slits 44, shown in FIGS. 10, 15 and 16, turn the strut sleeves 13, as shown in FIG. 14, into tension sleeves 14, whereby the tension screws 39 on the sleeve bearing 15 and the ball bearing 16, shown in the cross sections of FIGS. 15 and 16, create such a clamping friction connection that rigid adhesion of the coupling elements 17 and the screw sleeves 22 can be generated in their individual bearings.

Since the screw sleeve 22, as depicted in FIG. 17, is slit, it transfers the clamping force of the tension screws 39 to the strut spindle 12 to such an extent that it is even possible to establish overall torsional rigidity from the outer tension sleeve 14 to the inner strut spindle 12. Thus, thanks to the longitudinal screw-sleeve slits 23, it is possible to do without separate counter nuts, which would have given rise to all kinds of difficult assembly procedures.

FIG. 18 shows a longitudinal section of an alternative embodiment of the strut spindles 12. In this case, it is possible to do without the screw sleeve 22 since these spindles 12—hollowed out in order to reduce weight—can be fastened with a pivot-shaped insertable end having a ring groove 27 in the frame transverse bar 35, and in this form, the strut spindle 21 can be locked either rotatably or else torsion-free by means of a stud screw 38. Here again, the flange 24 and the insertion holes 26 serve to transfer the screw forces to the telescopic length adjustment of the struts.

FIGS. 19-22 show several views of a transport mechanism for the height adjustment or rod-wire bearings 32 supported on the strut-frame carriers 34. Cross pieces 43 hold the transport spindles 31 on the strut-frame carriers 34, and one or more adjustment nuts 33 can be affixed on this spindle. These height-adjustable adjustment nuts 33, to which the rod-wire bearings 32 are affixed, have the effect of a precisely adjustable shifting of the threaded wires 2. Such distance changes of the wire anchoring sites of the wires 2 of different levels in the same bone segment bring about tension regulations of the threaded wires 2 which, in turn, can have the effect of making it possible to somewhat shift one bone piece with respect to another adjacent bone piece.

It is also possible, without the use of a transport mechanism, to attach wire bearings 32 to the sections of the struts which form a longitudinal gap along the longitudinal strut axis 10 in such a way that they can either be slid or locked in place. In the case of changes in the strut lengths made by means of the telescopic strut bearings 13 with rod-wire bearings 32 held in such a way that they can shift, accompanying threaded wires 2 maintain their initial tension. In contrast, with the locking of the rod-wire bearings 32 and telescope operation of the strut bearings 13, depending on the telescope direction, biconvex or biconcave lateral bending of the threaded wires 2 with respect to each other occurs, since the lengthwise change of the struts occurs at a level between its anchors. This also makes it possible to somewhat slide one bone piece with respect to the adjacent bone piece.

FIGS. 23-26 show different views of the connection, which can be inserted, locked, rotated and affixed, of two frame-shaped strut sections with each other, whereby the design and function of the coupling axle 37 connecting these strut sections is shown. The relative rotatability of two strut sections coupled to each other in this manner leads to the possibility of putting these strut sections in rotated positions that differ from each other, thus making it possible to drill horizontal wires transfixing the bone at different levels in divergent directions.

Figure 27:
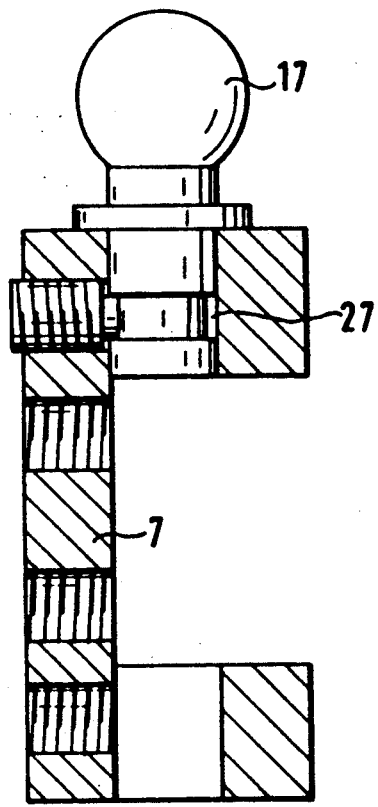
FIGS. 27–31 are views of perforated bearings, coupling elements and a ring-U-fastener.
Figure 28:
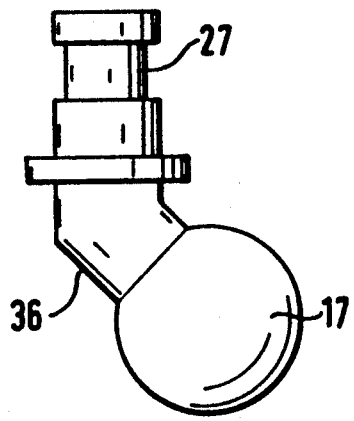

FIGS. 27 and 28 show that, by means of an angle 36 of the coupling elements 17, the assembly forms of the ring splint can be modified and therefore, that additional and more numerous pivoting arrangements can be implemented.

Figure 32:
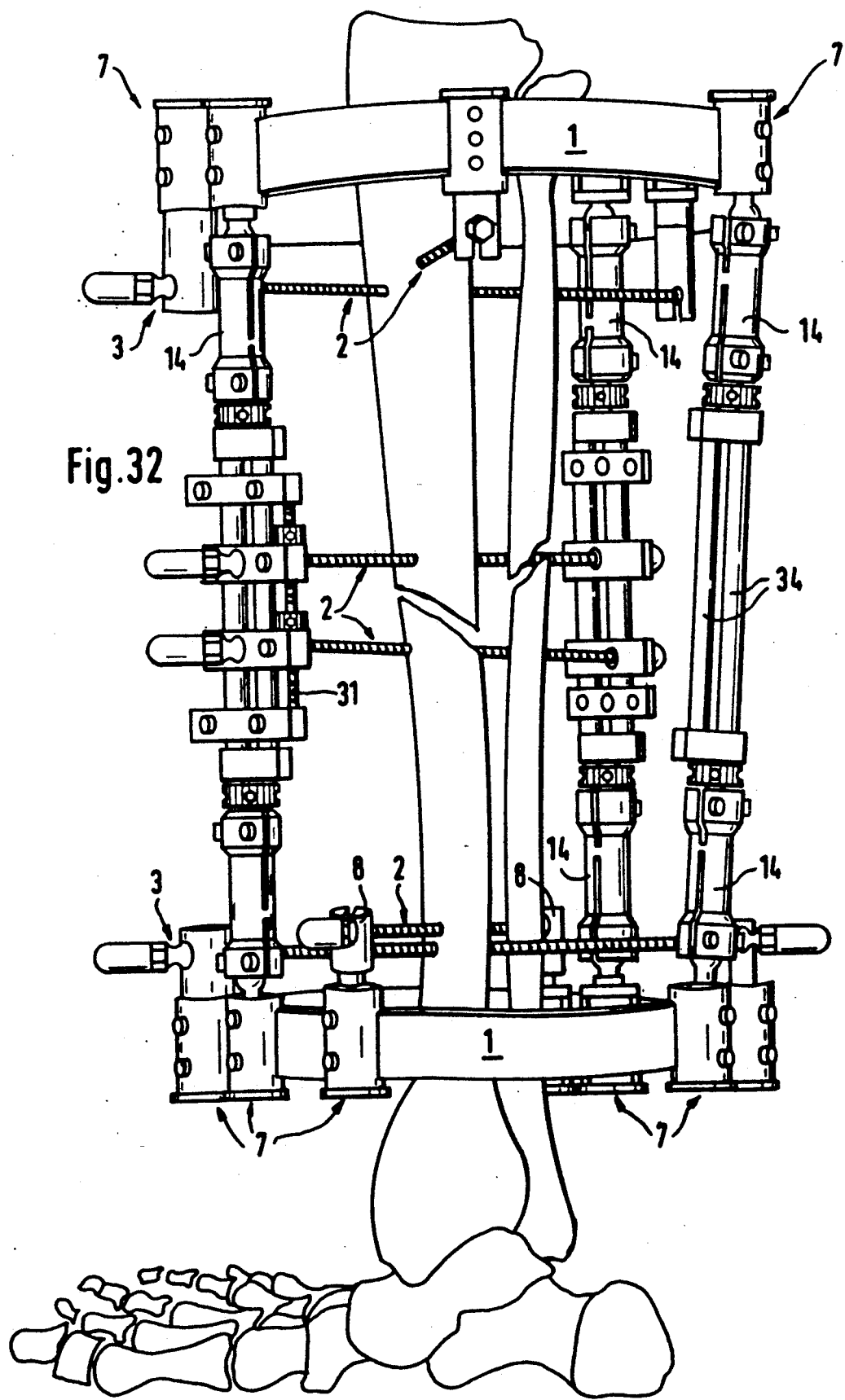
FIG. 32 is a spatial representation of a ring splint attached to the calf to set a broken tibia.

FIG. 32, a side view maintaining the reference numbers used so far, shows a ring splint fitted on a calf and consisting of two rings 1 and three struts using two transport mechanisms. This figure shows the spatial adjustment possibilities of all of the parts with respect to each other. Likewise, it can be seen from this figure that the ring splint according to the invention is a construction kit or building-block set that can be changed in many different ways.

The ring splint according to the invention can be used in bone surgery techniques for a large number of tasks.

It serves to treat bones, joints and soft parts for in-patient treatment as well as for operations and follow-up out-patient treatment.

In accident surgery, in orthopedics, in recovery surgery as well as in disaster, military and Third World medicine, this ring splint can be used especially to treat broken bones in the limbs, for limb traction, to heal damaged joints, to form new bone material in the case of congenital or acquired bone defects, to correct defective axial positions of the limbs and of the major body joints, to heal bone marrow infections, to remobilize stiff joints and for acute treatment in case of mass accidents in disaster areas, whereby in the latter case, the specific applications in abnormal emergency situations make it important to do without in-patient treatment and to avoid the need for general anesthesia.

A special range of applications lie in the safe auxiliary use of this ring splint in treating critical injuries of the type caused by explosions and shooting.

I claim:

1. A ring splint for setting and fixing bones and regulating stress in the same, comprising a pair of spaced, arcuate members each of which constitutes a ring or ring segment, said arcuate members having rectangular or square cross sections; a plurality of elongated struts connecting said arcuate members to one another and having respective longitudinal axes, each of said struts including a pair of tension sleeves, and each of said tension sleeves having a first bearing portion for adjustably coupling the associated strut to one of said arcuate members and a second bearing portion spaced from the respective first bearing portion, at least one bearing portion of each strut being designed to permit angular adjustment of the respective strut, and each of said struts further including an interchangeable, spindle-like element receivable in a respective second bearing portion for rotation relative thereto so as to adjust the length of the respective strut, each of said struts being provided with a slit-like gap which extends along the longitudinal axis thereof; a plurality of wires for holding a bone in a predetermined position, said wires being provided with continuous threads; a plurality of wire bearings each of which includes a U-shaped element designed to embrace one of said arcuate members in such a manner as to be shiftable along the respective arcuate member, each of said wire bearings a further including a perforated element having a passage for one of said wires, said U-shaped elements and perforated elements being provided with cooperating connecting portions for rotatably connecting a U-shaped element to the respective perforated element in a plug-like fashion, and each of said wire bearings also including a coupling element receivable in one of said first bearing portions to adjustably couple the respective wire bearing and arcuate member to a corresponding strut; a plurality of fasteners for clamping said U-shaped elements, perforated elements and spindle-like elements; and a plurality of nuts screwable onto said wires so as to tension and guide the same.

2. The splint of claim 1, wherein said nuts include pairs of position nuts having polyhedral peripheral surfaces for engagement with a bone, the position nuts of each pair being designed to abut one another when threaded onto one of said wires.

3. The splint of claim 1, wherein said nuts include tension nuts having spherical bearing surfaces and threaded end portions; and further comprising protective caps designed to be screwed onto said end portions.

4. The splint of claim 1, further comprising a plurality of elongated, threaded screw sleeves, each of said screw sleeves being receivable in one of said second bearing portions and being designed to receive one of said spindle-like elements, and each of said screw sleeves being provided with at least two longitudinal slits to permit the transmission of clamping forces from a tension sleeve to a spindle-like element by fasteners extending through the longitudinal slits.

5. The splint of claim 1, wherein each of said spindle-like elements is provided with a threaded portion, a flange having a surface or circular opening on the circumference thereof for reception of a key, and an annular groove for reception of a screw.

6. The splint of claim 1, further comprising locking elements for said U-shaped elements, each of said locking elements including a carrier plate and a pair of pins mounted on the carrier plate and extending perpendicular thereto, said pins having free ends provided with slits.

7. The splint of claim 1, further comprising additional wire bearings on said struts, threaded spindles connectible to said struts so as to extend in axial direction thereof, and adjusting nuts for adjustment of said additional wire bearings, said adjusting nuts being screwable onto said spindles.

8. The splint of claim 1, wherein each of said struts comprises a pair of elongated carriers extending parallel to the longitudinal axis of the respective strut; and further comprising a transverse frame element for each of said struts, each of said frame elements at least partly surrounding the associated carriers and defining a plane which is normal to the respective longitudinal axis, and each of said frame elements being connectible to an associated spindle-like element.

9. The splint of claim 1, wherein each of said coupling elements comprises two coupling sections having respective longitudinal axes which are inclined to one another.

10. The splint of claim 1, wherein each of said struts comprise two strut sections which are rotatable relative to one another; and further comprising a coupling for each of said struts connecting the respective strut sections to one another for rotation in opposite directions, each of said couplings being provided with an annular groove for reception of a clamping screw.

11. The splint of claim 1, wherein said arcuate members comprise fibers which are continuously and unidirectionally wound in circumferential direction of said arcuate members, said fibers having plastic sheaths and being embedded in a matrix.

* * * * *